US00PP09386P

United States Patent [19]

Iverson

[11] Patent Number: Plant 9,386

[45] Date of Patent: Nov. 28, 1995

[54] DAYLILY PLANT NAMED 'BURGUNDY LACE'

[76] Inventor: Ronald C. Iverson, Rte. 1, Box 326B, Orange, Va. 22960

[21] Appl. No.: 355,314

[22] Filed: Dec. 12, 1994

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new cultivar of daylily plant named Burgundy Lace, characterized by its very large, double and ruffled flowers each of which has 12 petals, main flower color of burgundy which merges into a deep yellow throat through a zone of deeper burgundy; very fragrant flowers, reblooming ability, and its floriferous habit.

2 Drawing Sheets

The present invention comprises a new and distinct cultivar of daylily which belongs to the genus Hemerocallis, and is hereinafter referred to by the cultivar name Burgundy Lace.

The new cultivar is the result of an open pollination breeding program in which numerous unnamed and unidentified daylily cultivars were planted in an open cultivated field in a controlled environment in Merriville, Ind. Seed was collected from the open pollinated female plants and grown in a controlled area in Merriville, Ind.

Well over one thousand seedlings plants were mass-selected in early summer 1990, and grown out in Long Grove, Ill. in a cultivated area. The new cultivar was discovered and selected from the mass-selected plants by inventor Ronald C. Iverson in August 1980 in such area in Long Grove, Ill.

The first act of asexual reproduction of Burgundy Lace was accomplished when divisions were taken from the selection in September 1990 in a controlled environment in Long Grove, Ill. by Ronald C. Iverson. Horticulture examination of selected units initiated in June 1991 has demonstrated that the combination of characteristics as herein disclosed for Burgundy Lace are firmly fixed and are retained through successive generations of asexual reproduction.

Burgundy Lace has not been observed under all possible environmental conditions. The phenotype may vary significantly with varitions in environment such as temperature, light intensity, and daylength without, however, any variance in genotype. The following observations, measurements, and comparisons describe plants grown in Long Grove, Ill. under greenhouse conditions which approximate those generally used in commercial practice.

The following traits have been repeatedly observed and are determined to be basic charactertistics of Burgundy Lace which in combination distinguish this daylily as a new and distinct cultivar.

1. The flowers have three distinct color zones on the outer and inner petals, with the sepals having only two colors.

2 . Flowers are very fragrant.

3. Flowers are very ruffled and have six (6) extra petals, making it a double flower.

4. Individual flowers are very large, being approximately 5½ inches in diameter. There are about 16 buds on an average flowering scape, making the new cultivar very floriferous.

5. Flowers are sun resistant and do not fade in bright light.

6. Individual fans produce 2–3 flowering scapes in each season. This ability to rebloom is a significant feature of the new cultivar.

7. Plants of the new cultivar are vigorous and healthy, and flowers are borne well above the foliage.

The accompanying color photographic drawings show typical flower characteristics of Burgundy Lace, with colors being as true as possible with illustrations of this type.

The photo on sheet 1 is a top perpective view of a typical plant of the new cultivar grown in a 10 inch pot.

The photo on sheet 2 is a greatly enlarged top view showing in much greater detail the flower parts.

In the following description, color references are made to The Royal Horticultural Society Colour Chart. The color values were determined between 2:00 to 2:30 p.m. on June 12 under full sunlight conditions at Long Grove, Ill.

Parentage:

*Origin.*—Selection from mass-selected seedling population obtained by open pollination.

*Parentage.*—Seed parent: Unknown. Pollen parent: Unknown.

Classification:

*Botanic.*—Hemerocallis hybrid.

*Commercial.*—Large flower double daylily. cv. Burgundy Lace.

Plant description:

*Form.*—Wide, spreading.

*Height.*—Approximately 19 inches.

*Growth habit.*—Clump forming, vigorous.

*Strength.*—Moderate.

*Foliage.*—Quantity: Average. Size of leaf: 1¼ inches wide×22 inches long. Shape of leaf: Typical Hemerocallis. Texture: Smooth. Color: Green 144A.

*Bulbs.*—Size: 5 inches long. Color: Tan.

Bud description:

*Form.*—Fat, columnar.

*Size.*—3 inches long.

*Opening.*—Early morning.

*Color.*—Green streaked with purple 59B.

Flowering description:

*Blooming habit.*—Late June until October.

*Size.*—Very large, 5½ inches in diameter.

*Borne.*—15° angle from the scape.

*Shape.*—Round.

*Tepalage.*—Number of tepals: 12. Arrangement: Star. Color: Upper surface: Main color 178A blending through zone of 185A to throat 9A; inner petals have gold margins and 3 outer petals have edges darker than main color. Lower surface: 15C darkening to 166A on edge. Tepal longevity: One day. Spotting: No markings. Color change: Color is very persistent with no or very little fading even on hot days. Involucre: Smooth and shiny with crimped edges. Sepals: Appear diamond dusted overlaid with burgundy. Disease resistance: No recognized problem.

Fragrance: Slightly sweet fragrance. Lasting quality: One day, 6 a.m. to 10 p.m.

Reproductive organs:

*Stamens, anthers.*—Arrangement: Central. Number: Two, the rest are modified into petals. Filaments: Yellow.

*Pistils.*—2½ inches in length.

Fruit:

*Fertility.*—Not very fertile.

*Shape.*—Round.

*Color at maturity.*—Black.

I claim:

1. A new and distinct cultivar of daylily plant named Burgundy Lace, as illustrated and described.

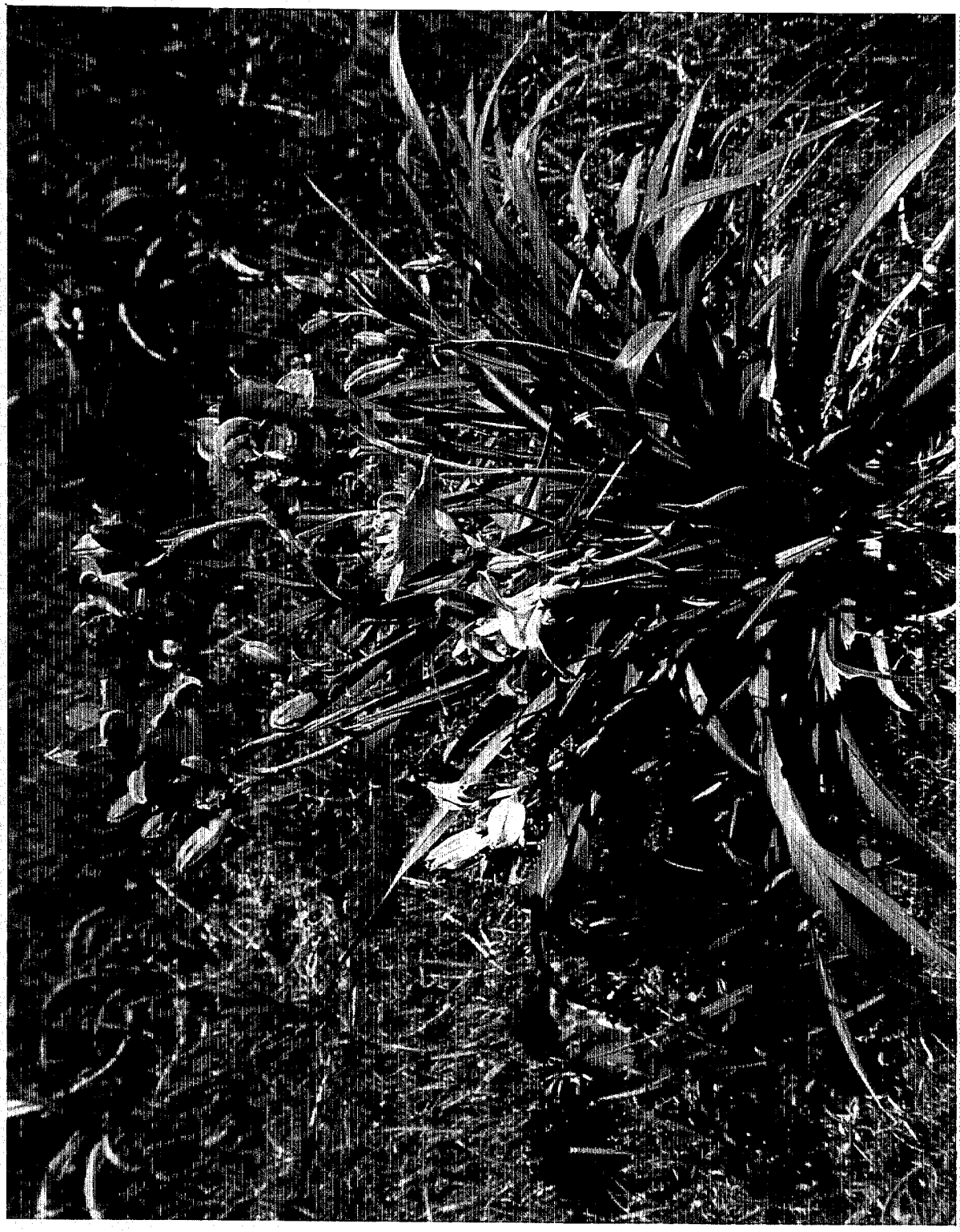

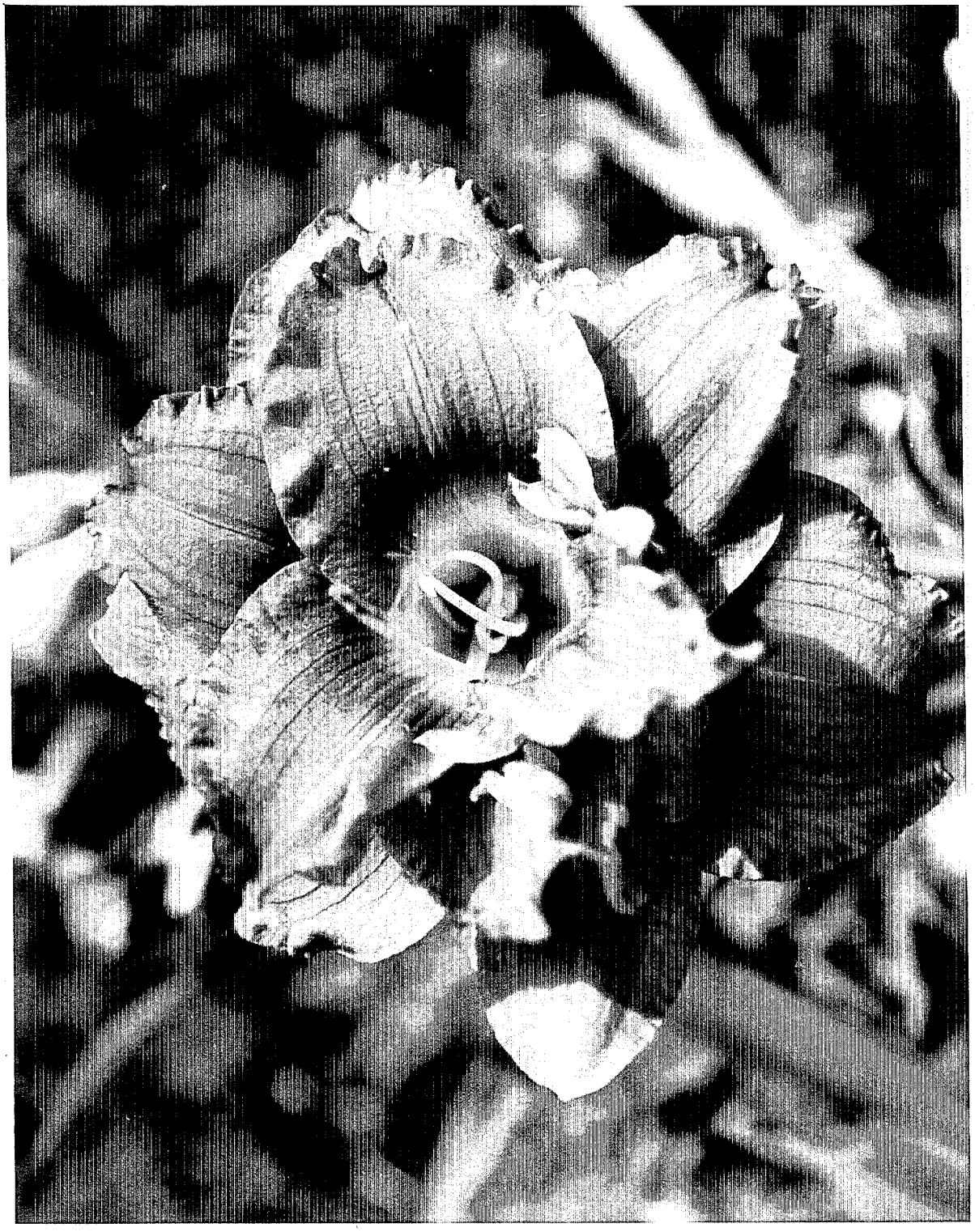

* * * * *